US008759065B2

(12) United States Patent
Asenjo et al.

(10) Patent No.: US 8,759,065 B2
(45) Date of Patent: Jun. 24, 2014

(54) PROTEIN AND DNA SEQUENCE ENCODING A COLD ADAPTED SUBTILISIN-LIKE ACTIVITY

(75) Inventors: Juan A. Asenjo, Santiago (CL); Barbara A. Andrews, Santiago (CL); Juan Pablo Acevedo, Mulheim (DE); Fernando Reyes, Santiago (CL); Luis O. Burzio, Santiago (CL)

(73) Assignee: University of Chile, Santiago (CL)

( * ) Notice: Subject to any disclaimer, the term of this patent is extended or adjusted under 35 U.S.C. 154(b) by 700 days.

(21) Appl. No.: 12/672,226

(22) PCT Filed: Aug. 6, 2008

(86) PCT No.: PCT/US2008/072280
§ 371 (c)(1),
(2), (4) Date: Feb. 4, 2010

(87) PCT Pub. No.: WO2009/021000
PCT Pub. Date: Feb. 12, 2009

(65) Prior Publication Data
US 2012/0264191 A1    Oct. 18, 2012

Related U.S. Application Data

(60) Provisional application No. 60/954,198, filed on Aug. 6, 2007.

(51) Int. Cl.
*C12N 9/48* (2006.01)
*C12N 15/63* (2006.01)
*C07H 21/04* (2006.01)
*C12N 1/20* (2006.01)

(52) U.S. Cl.
USPC .............. 435/212; 435/320.1; 435/252.3; 536/23.2

(58) Field of Classification Search
None
See application file for complete search history.

(56) References Cited

U.S. PATENT DOCUMENTS 5,217,878 A    6/1993    van Eekelen et al.
5,278,062 A    1/1994    Samal et al.

OTHER PUBLICATIONS

Wishart et al, A single mutation converts a novel phosphotyrosine binding domain into a dual-specificity phosphatase. J Biol Chem. Nov. 10, 1995;270(45):26782-26785.*
Whisstock et al, Prediction of protein function from protein sequence and structure. Q Rev Biophys. Aug. 2003;36(3):307-40. Review.*
Allen, The catalytic function of active site amino acid side chains in well-characterized enzymes. Ann NY Acad Sci. 1981;367:383-406.*
Patrick et al, User-friendly algorithms for estimating completeness and diversity in randomized protein-encoding libraries. Protein Eng. Jun. 2003;16(6):451-7.*
Miyake, R. et al. 'Construction of a low temperature protein expression system using a cold-adapted bacterium, *Shewanella* sp. Strain Ac10, as the host.' Appl Environ Microbiol. vol. 73(15), pp. 4849-4856, online publication on May 25, 2007.
Acevedo J.P. et al. 'Cloning of complete genes for novel hydrolytic enzymes from Antarctic sea water bacteria by use of an improved genome walking technique.' J Biotechnol. vol. 133(3), pp. 277-286. Feb. 1, 2008.

* cited by examiner

*Primary Examiner* — Sheridan Swope
(74) *Attorney, Agent, or Firm* — Mendelsohn, Drucker & Dunleavy, P.C.

(57) ABSTRACT

Nucleic acid and corresponding amino acid sequences of a cold adapted subtilisin-like activity protein, insolated from antarctic marine origin, preferably from an Antarctic bacteria (*Polaribacter* sp) that can be used in a variety of industrial contexts and commercial purposes including laundry detergents, food processing, leather processing and skin care products. Nucleic acid constructs, vectors, and host cells comprising the nucleic acid sequences as well as methods for producing and using the cold adapted subtilisin-like protein are also described.

13 Claims, No Drawings

US 8,759,065 B2

PROTEIN AND DNA SEQUENCE ENCODING A COLD ADAPTED SUBTILISIN-LIKE ACTIVITY

BACKGROUND OF THE INVENTION

1. Field of the Invention

The present invention relates to purified nucleic acids encoding Antarctic bacteria (*Polaribacter* sp.) derived enzymes such as proteinases, which can be a protein, and to purified polypeptides that have high proteolytic activity and belong to the superfamily of subtilisin-like enzymes (subtilases). The present invention also relates to a protein having cold adapted activity, especially specific activity in the range around 4-45° C., and having noticeable activity in the range of 4-20° C. In addition, the present invention relates to a DNA construct comprising a DNA sequence encoding the cold adapted subtilisin-like protease, and a cell including the DNA construct. Furthermore, the present invention relates to a method of preparing the cold adapted subtilisin-like protease by use of recombinant DNA techniques.

2. Description of the Prior Art

The subtilisin-like serine protease (S8) family plays roles in a multitude of diverse bacterial cellular and metabolic processes, such as sporulation and differentiation, protein turnover, maturation of enzymes and hormones and maintenance of the cellular protein pool. Another important function, especially for extracelullar subtilisin-like proteasas, is the hydrolysis of proteins in external cell environments which enables the cell to absorb and utilize hydrolytic products.

Serine proteases are used in numerous and varied industrial contexts and commercial purposes including laundry detergents, food processing, leather processing, medical usage and skin care products. In laundry detergents, the protease is employed to break down organic or poorly soluble compounds to more soluble forms that can be more easily dissolved in detergent and water. Examples of food processing include tenderizing meats, preparation of protein hydrolyzates and maturing cheese. In the case of medical usage, proteases are applied to treat of burns, purulent wounds, furuncles and deep abscesses. Proteases may be included in skin care field to remove scales on the skin surface that build up due to an imbalance in the rate of desquamation.

Common proteases used in some of these applications are derived from prokaryotic or eukaryotic cells that are easily grown for industrial manufacture of their enzymes. For example a common species used is *Bacillus* as described in U.S. Pat. No. 5,217,878. Alternatively, U.S. Pat. No. 5,278, 062 describes serine proteases isolated from a fungus, *Tritirachium album*, for use in laundry detergent compositions. The advent of recombinant technology allows expression of any species' proteins in a host suitable for industrial manufacturing. The majority of the commercially available proteases used in detergent applications have high optimal temperatures, for example 60° C. Bacteria isolated from cold environments such as Antarctic sea water are psychrophilic microorganisms and are expected to have cold adapted enzymes.

There are some enzymes with cold adapted subtilisin-like activity from psychrophilic microorganisms, for example: *Flavobacterium balustinum* (Morita, Y., Hasan, Q., Sakaguchi, T., Murakami Y., Yokohama, K., Tamaya, E. (1998) Appl. Microbiol. Biotechnol. 50:669-675), *Bacillus* TA41 (Davial, S., Feller, G., Narinx, E., Gerday, Ch. (1994) J. Biol. Chem. 269:17448-17453) and *Pseudomonas* strain DY-A (Zeng, R., Zhang, R., Zhao, J., Lin, N. (2003) Extremophiles 7:335-337). All of these proteins have low stability at ambient temperatures and in the presence of common compounds present in commercial detergents.

Therefore, there is a need for new alternative proteases, in this case subtilisin-like proteases which work at ambient and low temperatures and in the presence of common commercial detergent compositions.

SUMMARY OF THE INVENTION

The present invention relates to cold-adapted proteases which can be isolated from the supernatant liquid of a culture of a *Polaribacter* sp., a method of purification of the above-mentioned cold-adapted protease from *Polaribacter* sp. strain 3-17 and a method for isolation of the complete nucleic acid sequence which encodes the *Polaribacter*-derived cold adapted subtilisin-like protein.

One embodiment of the present invention is a substantially pure nucleic acid comprising a nucleic acid encoding a polypeptide having at least about 85% homology (such as identity) to a *Polaribacter*-derived cold adapted subtilisin-like protein or a reference protein, such as the polypeptide of SEQ ID NO: 2, and more preferably, at least about 90% homology, and even more preferably, at least about 95% homology. The level of homology (such as identity) applies to all embodiments of the invention.

In certain embodiments, the substantially pure nucleic acid comprises an engineered nucleic acid variant encoding a polypeptide differing from a reference protein or a *Polaribacter*-derived cold adapted subtilisin like protein by no more than about 30 amino acid substitutions, and more preferably, no more than about 20 amino acid substitutions. Preferably, the engineered substitutions cause a conservative substitution in the amino acid sequence of a reference sequence or a cold adapted protein.

The invention additionally includes vectors capable of reproducing in a cell, such as a eukaryotic or prokaryotic cell, a nucleic acid identical to sequence of SEQ ID NO: 1 as well as transformed cells having such a nucleic acid.

Another embodiment of the invention is a transformed cell, such as a prokaryotic or eukaryotic cell, comprising a nucleic acid encoding a polypeptide having at least about 85% homology to a reference sequence or a *Polaribacter*-derived cold adapted subtilisin like protein. Preferably, the transformed cell expresses one of the enzymes described herein.

Yet another embodiment of the invention is a vector capable of reproducing in a cell such as a eukaryotic or prokaryotic cell. The vector comprises a nucleic acid encoding a polypeptide having at least about 85% homology to a reference sequence or a *Polaribacter*-derived cold adapted subtilisin-like protein SEQ ID NO: 2. Preferably, the vector of the invention codes for expression, intracellularly or extracellularly, of the cold adapted subtilisin-like protein described herein.

Another embodiment of the present invention is a polypeptide comprising a substantially pure isoform of a reference sequence or a *Polaribacter*-derived cold adapted subtilisin-like protein or engineered variant thereof, and preferably, a polypeptide comprising SEQ ID NO: 2.

The invention further provides a cleaning or detergent composition comprising the polypeptide or the cold adapted subtilisin-like protein of the invention Yet another embodiment of the invention is a method of preparing an enzyme such as a cold adapted subtilisin-like enzyme, wherein the protein has at least about 85% homology to a reference sequence or a *Polaribacter*-derived multifunctional protein. Such method comprises:

1. Constructing a recombinant chimeric expression vector, comprising a nucleic acid sequence of the present invention such as SEQ ID NO: 1.
2. Transforming an appropriate eukaryotic or prokaryotic host cell with the expression vector for expressing, intracellularly or extracellularly, a nucleic acid encoding the protein; and
3. Growing the transformed cell in culture and isolating the protein from the transformed cell or the culture medium.

These, together with other objects and advantages which will become subsequently apparent reside in the detailed construction and operation as more fully hereinafter described and claimed.

DETAILED DESCRIPTION OF EMBODIMENTS OF THE INVENTION

Although only certain embodiments of the invention are explained in detail, it is to be understood that the invention is not limited in its scope to the details set forth in the following description. The invention is capable of other embodiments and of being practiced or carried out in various ways. Also, in describing these embodiments, specific terminology will be resorted to for the sake of clarity. It is to be understood that each specific term includes all technical equivalents which operate in a similar manner to accomplish a similar purpose.

For the purposes of this application, the terms listed below shall have the following meaning:

"Isoform" refers to a naturally occurring sequence variant of a substantially homologous protein within the same organism. Preferably, the Isoform shares at least about 85% identity, and more preferably, at least about 90% identity with one of the following sequences of amino acid residues:
  amino acid residues 25-1129 of SEQ ID NO: 2.
  amino acid residues 96-1129 of SEQ ID NO: 2.
  amino acid residues 96-870 of SEQ ID NO: 2.
  amino acid residues 96-650 of SEQ ID NO: 2.
  amino acid residues 96-560 of SEQ ID NO: 2.

"Polaribacter-derived cold adapted subtilisin like activity protein" refers to a cold adapted subtilisin-like protein having the same sequence as a protein isolated from Polaribacter sp. strain 3-17 and having the properties of the protein described in the section entitled "Preferred Characteristics of the Cold Adapted Subtilisin like Protein." The amino acid sequence included in SEQ ID NO:2 or other isoforms thereof or chimeric polypeptides thereof are examples of Polaribacter-derived cold adapted subtilisin-like activity proteins.

"Percent sequence identity" refers to the percentage of two sequences that are deemed identical or homologous within the skill of the art. To determine the percent identity of two amino acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). Alignment for purposes of determining percent amino acid sequence identity can be achieved in various ways that are within the skill of the art, for example, using publicly available computer software such as BLAST-2 software that are set to their default parameters. Those skilled in the art can determine appropriate parameters for measuring alignment, including any algorithms needed to achieve maximal alignment over the full length of the sequences being compared. The ClustalW (1.60) alignment method is used in this application.

"Polypeptide" refers to a polymer made up of amino acids linked together to form peptide bonds, preferably forming a pre-pro-protein, pro-protein, protein or fragment thereof.

"Pre-pro-protein" refers to a polypeptide consisting of a signal sequence, pro-regions, and a processed protein sequence.

"Pro-protein" refers to a polypeptide consisting of pro-regions and processed protein sequence.

"Genome walking method" refers to a technique for isolating polynucleotide of unknown sequence regions on either side of known ones; they are collectively known as genome walking or chromosome walking techniques.

"Polynucleotide" refers to a polymer of DNA or RNA which can be single- or double-stranded, optionally containing synthetic, non-natural or altered nucleotide bases capable of incorporation into DNA or RNA polymers. The polynucleotide may be in the form of a separate fragment or as component of a larger nucleotide sequence construct.

Purification of Native Polaribacter-Derived Cold Adapted Subtilisin Like Activity Protein The native polypeptide embodiments of the invention are preferably the protease produced by the use of microorganisms belonging to Polaribacter genus. One example of the microorganisms having the ability to produce the protease according to the present invention is a Polaribacter sp. strain 3-17 which was isolated from seawater collected at Frei Montalva Base (Lat 62° 11" S Long 58° 58" W), King George Island, Chilean Antarctic. This strain was characterized by the nucleic acid sequence of its 16S rRNA gene which is identical to sequence of SEQ ID NO: 19.

The conditions for culturing the strain in this invention may be diverse, so far as they permit good production of the protease. For example: a solid or liquid medium may be used, a shaken culture or an aeration spinner culture, different carbon sources (glucose, trehalose, fructose, maltose sucrose, starch and malt oligo-saccharide), different nitrogen sources (peptone, yeast extract, malt extract, meat extract, soybean powder, cotton seed powder, amino acids and nitrates), different inorganic salts (magnesium, phosphate, calcium, sodium, potassium, iron and manganese) and other necessary nutrients. Culturing conditions such as the pH and temperature can also be suitably altered. In this invention the preferred conditions are neutral pH and a culture temperature of about 10° C.

The protease of the present invention is preferably present in the supernatant of the culture medium, but is also present in cell walls of bacteria. The protease may be used in any form such as bacterial cells, as a crude enzyme obtained from the bacterial cells or the supernatant of the culture medium, or as an extracted and purified enzyme. Alternatively, a protease immobilized by a known method can be also used. Since the protease of the present invention is found mainly in the extracellular medium, a crude enzyme solution can easily be obtained by removing the bacterial cells with the aid of filtration or centrifugation. This crude enzyme can be further purified by a known purification method or combination of known methods. Typical embodiments of suitable purification methods are described in the examples herein.

Polynucleotides and Polypeptides

The polynucleotide embodiments of the invention are preferably deoxyribonucleic acids (DNAs), both single- and double-stranded, and most preferably double-stranded deoxyribonucleic acids. However, they can also be, without limitation, ribonucleic acids (RNAs), as well as hybrid RNA:DNA double-stranded molecules.

The present invention encompasses polynucleotides encoding a Polaribacter-derived cold adapted subtilisin like activity protein, whether native or synthetic, RNA, DNA, or cDNA, that encode the protein, or the complementary strand thereof, including, but not limited to, nucleic acids found in a cold adapted subtilisin-like protein-expressing organism. For recombinant expression purposes, codon usage preferences for the organism in which such a nucleic acid is to be expressed are advantageously considered in designing a synthetic cold adapted subtilisin like protein-encoding nucleic acid.

The nucleic acid sequences can be further mutated, for example, to incorporate useful restriction sites. See Sambrook et al. Molecular Cloning, a Laboratory Manual (Cold Spring Harbor Press, 1989). Such restriction sites can be used to create "cassettes", or regions of nucleic acid sequence that are easily substituted using restriction enzymes and ligation reactions. The cassettes can be used, for example, to substitute synthetic sequences encoding mutated cold adapted subtilisin like protein amino acid sequences.

The nucleotide sequences of the present invention may comprise:
  a) SEQ ID NO: 1 or a degenerative variant thereof; or
  b) positions 73-3390 of SEQ ID NO: 1 or a degenerative variant thereof; or
  c) positions 286-3390 of SEQ ID NO: 1 or a degenerative variant thereof; or
  d) positions 286-2610 of SEQ ID NO: 1 or a degenerative variant thereof; or
  e) positions 286-1950 of SEQ ID NO: 1 or a degenerative variant thereof; or
  f) positions 286-1680 of SEQ ID NO: 1 or a degenerative variant thereof.

The nucleic acid sequences of the present invention can encode, for example, one of several isoforms of a *Polaribacter*-derived cold adapted subtilisin like activity protein.

This *Polaribacter*-derived cold adapted subtilisin-like activity protein corresponds to a pre-pro-protein. The signal sequence of pre-pro-protein is the segment of the protein that is present in the precursor protein in the bacterial cell but absent in the protein after secretion to the extracellular environment. The signal sequence corresponds to amino acid residues 1-24 in SEQ ID NO: 2: Met Lys Lys Arg Tyr Ile Asn Leu Leu Leu Thr Ile Gly Val Phe Met Ile Ser Ala Phe Asn Met Asn Ala. The remaining amino acid sequences of the polypeptides represent the pro-protein. The pro-proteins, especially in extracellular proteases, are preferably present in an inactive form or partially active form and can transform into an active protein through the auto-digestion or extraction of pro-regions, those pro-regions often correspond to the initial region, final region or both regions of the pro-protein sequence. The pro-regions of the *Polaribacter*-derived cold adapted subtilisin-like activity protein are:
  1. amino acid residues 25-95 in SEQ ID NO: 2.
  2. amino acid residues 871-1129 in SEQ ID NO: 2.
  3. amino acid residues 651-870 in SEQ ID NO: 2.
  4. amino acid residues 561-650 in SEQ ID NO: 2.
The remaining amino acid sequences of these polypeptides (other than the signal sequence and pro-protein segments) represent the processed protein.

Various embodiments of the *Polaribacter*-derived cold adapted subtilisin-like activity protein, include, but are not limited to, an amino acid sequence as shown in SEQ ID NO: 2; as well as positions 96-1129 of SEQ ID NO: 2, positions 96-870 of SEQ ID NO: 2, positions 96-650 of SEQ ID NO: 2 and positions 96-560 of SEQ ID NO: 2 which could be individually proteolytically active. Additional embodiments of the *Polaribacter*-derived cold adapted subtilisin-like activity protein comprise amino acid sequences which form part of the "catalytic triad" of SEQ ID NO: 2, i.e. positions 121-141, 156-176 and 347-367 of SEQ ID NO:2. Stated another way, such embodiments comprise nucleotide sequences 361-423, 466-528, 1039-1101 of SEQ ID NO: 1. Other embodiments of the *Polaribacter*-derived cold adapted subtilisin-like activity protein comprise amino acid sequences which are recognized as fibronectin type 3 domains in SEQ ID NO: 2, i.e. positions 651-870 and 561-650 of SEQ ID NO: 2. Such embodiments comprise nucleotide sequences 1951-2610 and 1681-1950 of SEQ ID NO: 1 respectively. These fibronectin domains could be helpers for the proteolytic efficiency against some substrates or helpers in protein refolding and processing.

Preferably, the nucleic acids will encode polypeptides having at least 85% homology, more preferably, at least 90% homology, even more preferably, at least about 95% homology to a reference protein or a *Polaribacter*-derived cold adapted subtilisin like protein, such as the polypeptides of SEQ ID NO: 2 or other naturally occurring isoforms.

The processed protein of the polypeptide of SEQ ID NO:2 is about 62% identical to the subtilisin-like serine proteinase in the *Psychroflexus torquis* ATCC 700755 according to the sequence provided by Genbank (Mountain View, Calif.), database acquisition no. ZP_01253004, and about 43% identical to the subtilisin-like serine protease in the *Flavobacterium bacterium* BBFL 7, according to the sequence provided by Genbank, database acquisition no. ZP_01202744, and about 30% identical to the alkaline serine protease in the *Bacillus* sp. Ksm-Kp43, according to the sequence provided by Protein Data Bank, database acquisition no. 1 WMDA. Preferably, the nucleic acids encoding polypeptides having cold adapted subtilisin-like activity are less than about 80% identical to the above-identified proteinases of *Psychroflexus torquis* ATCC 700755, *Flavobacterium bacterium* BBFL7 or *Bacillus* sp. Ksm-Kp43.

The cold adapted subtilisin-like protein-encoding sequence can be, for instance, substantially or fully synthetic. For recombinant expression purposes, codon usage preferences for the organism in which such a nucleic acid is to be expressed are advantageously considered in designing a synthetic cold adapted protein-encoding nucleic acid. Since the nucleic acid code is degenerate, numerous nucleic acid sequences can be used to create the same amino acid sequence. This natural "degeneracy" or "redundancy" of genetic code is well known in the art. It will thus be appreciated that the nucleic acid sequence shown in the Sequence Listing provide only an example within a large but definite group of nucleic acid sequences that will encode the relevant polypeptides as described herein.

Polypeptides of the present invention preferably include all polypeptides encoded by the nucleic acids having the sequence identical to SEQ ID NO: 1 or its degenerate variants thereof, and all polypeptides comprising the amino acid sequences shown as:
  a) amino acid residues 25-1129 of SEQ ID NO: 2.
  b) amino acid residues 96-1129 of SEQ ID NO: 2.
  c) amino acid residues 96-870 of SEQ ID NO: 2.
  d) amino acid residues 96-650 of SEQ ID NO: 2.
  e) amino acid residues 96-560 of SEQ ID NO: 2.
as well as all obvious variants of these peptides that are within the art to make and use. In addition, the polypeptides according to the present invention have, preferably at least about 85% sequence identity, also preferably at least about 90% sequence identity, more preferably at least 95% sequence identity, also more preferably at least 96% sequence identity, even preferably at least 97% sequence identity, even more preferably at least about 98% sequence identity, still preferably at least 99% sequence identity to the amino acid sequence selected from:
  a) amino acid residues 25-1129 of SEQ ID NO: 2.
  b) amino acid residues 96-1129 of SEQ ID NO: 2.
  c) amino acid residues 96-870 of SEQ ID NO: 2.
  d) amino acid residues 96-650 of SEQ ID NO: 2.
  e) amino acid residues 96-560 of SEQ ID NO: 2.

Methods of Synthesizing Polypeptides

Expression Vectors

The present invention also relates to recombinant expression vectors comprising a nucleic acid sequence of the present invention, a promoter, and transcriptional and translational stop signals. The nucleic acid sequence of the present invention may be expressed by inserting the nucleic acid sequence or a nucleic acid construct comprising the sequence as identified in SEQ ID NO: 1 into an appropriate vector for expression. In creating the expression vector, the coding sequence, as identified in SEQ ID NO: 1, is located in the vector so that it is operably linked with the appropriate control sequences for expression.

The recombinant expression vector may be any vector (e.g., a plasmid) which can be conveniently subjected to recombinant DNA procedures and can bring about the expression of the nucleic acid sequence. The choice of the vector will typically depend on the compatibility of the vector with the host cell into which the vector is introduced. The vectors may be linear or closed circular plasmids.

The vector may be an autonomously replicating vector, i.e., a vector which exists as an extra chromosomal entity and its replication is independent of chromosomal replication, e.g., a plasmid, an extra chromosomal element, a mini chromosome, or an artificial chromosome. The vector may contain any means for assuring self-replication. Alternatively, the vector may be one which, when introduced into the host cell, is integrated into the host cell's genome and replicated together with the chromosome(s). Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene whose expression product provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. The amdS and pyrG genes of *Aspergillus nidulans* or *Aspergillus oryzae* and the bar gene of *Streptomyces hygroscopicus* are preferred for use in an *Aspergillus* cell.

The vectors of the present invention preferably contain an element(s) that permits stable integration of the vector into the host cell's genome or autonomous replication of the vector in the cell independent of the genome.

For integration into the host cell genome, the vector may rely on the nucleic acid sequence encoding the polypeptide or any other element of the vector for stable integration of the vector into the genome by homologous or non-homologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAM.beta.1 permitting replication in *Bacillus*. Examples of origins of replication for use in a yeast host cell are the 2 micron origin of replication, ARS1, ARS4, the combination of ARS1 and CEN3, and the combination of ARS4 and CEN6.

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the present invention for the recombinant production of the polypeptides.

A vector comprising a nucleic acid sequence of the present invention is introduced into a host cell so that the vector is maintained as a chromosomal integrant or as a self-replicating extra-chromosomal vector as described earlier. The choice of a host cell will, to a large extent, depend upon the gene encoding the polypeptide and its source.

The host cell may be a unicellular microorganism, e.g., a prokaryote and unicellular eukaryote (yeast), or a non-unicellular organism, e.g., a eukaryote.

Useful unicellular cells are bacterial cells such as gram positive bacteria including, but not limited to, a *Bacillus* cell, e.g., *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus, Bacillus licheniformis, Bacillus stearothermophilus,* or *Bacillus subtilis* cell. In another preferred embodiment, the *Bacillus* cell is an alkalophilic *Bacillus*.

The introduction of a vector into a bacterial host cell may, for instance, be achieved by protoplast transformation through electroporation or conjugation, using competent cells.

The host cell may be a eukaryote, such as a mammalian, insect, plant, or fungal cell. In a preferred embodiment, the host cell is a fungal cell. "Fungi" as used herein includes the phyla Ascomycota, Basidiomycota, Chytridiomycota, and Zygomycota as well as the Oomycota and all mitosporic fungi.

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes).

In an even more preferred embodiment, the yeast host cell is a *Candida, Hansenula, Kluyveromyces, Pichia, Saccharomyces, Schizosaccharomyces,* or *Yarrowia* cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell.

Production

The present invention also relates to a method for producing a polypeptide of the invention, the method comprising (a) cultivating a recombinant host cell as described above under conditions conducive to the production of the polypeptide, and (b) recovering the polypeptide from the cells and/or the culture medium.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermenters performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions. If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989). The polypeptides of the present invention may need additional purification. Techniques are applied as needed, including without limitation, FPLC (Pharmacia, Uppsala, Sweden), HPLC (e.g., using gel filtration, reverse-phase or mildly hydrophobic columns).

Preferred Characteristics of Cold Adapted Subtilisin-like Protein

Antarctic Bacteria, including without limitation Bacteria of the genus *Polaribacter*, is the preferred source of *Polaribacter*-derived cold adapted subtilisin like proteins.

Preferably, the protein has a molecular weight between about 45 kd and about 115 kd, and more preferably from about 48 kd to about 61 kd, and most preferably about 52 kd, as determined by sodium dodecyl sulfate ("SDS") polyacrylamide gel electrophoresis ("PAGE"). Further, the protein preferably has substantial homology to a *Polaribacter*-derived cold adapted subtilisin-like protein. Preferred proteins are hydrolases, and preferably, proteases.

Protease activity can be determined by incubating a protein preparation with succinylated casein (concentration 1% w/v in sodium borate 50 mM, pH 8.0) at 20° C. for 30 minutes and measuring the release of amino acids or the appearance of new NH2 groups using 2,4,6-trinitrobenzene sulfonic acid (TNBSA). Interaction between TNBSA and NH2 groups can be detected at 340-450 nm (Baragi, V. et al. (2000). *Matrix. Biol.* 19: 267-273).

Subtilisin-like activity can be determined by the method of Erlanger et al (Erlanger, B. F., N. Kokowsky, and W. Cohen. (1961). *Arch. Biochem. Biophys.* 95:271-278). This method consists of the measurement of the degradation of Succinyl-Ala-Ala-Pro-Phe-p-Nitroanilide (Succ-AAPF-pNa) in 50 mM Tris HCl pH 8.0 and 2 mM $CaCl_2$ for 20 minutes at 20° C. Released p-Nitroanilide groups can be detected by their preferable absorbance at 410 nm.

Preferably, the pH optimum of the cold adapted protein is substrate dependent. For the substrate succinilated casein, the pH optimum is preferably from about 5 to about 12, more preferably, from about 6 to about 10. For the substrate Succ-AAPF-pNa, the pH optimum is preferably from about 7 to about 9, more preferably in excess of about 8.0.

Preferably, the cold adapted subtilisin-like protein of the invention has a temperature optimum for activity against succinilated casein and against Succ-AAPF-pNa in the range of about 40° C. to about 50° C. The cold adapted subtilisin-like protein still shows high activity at low temperatures (4-20° C.), using both substrates.

Use in Detergent

The polypeptide of the invention may be added to and thus become a component of a detergent composition, (U.S. Pat. No. 5,693,520).

The detergent composition of the invention may for example be formulated as a hand or machine laundry detergent composition that includes a laundry additive composition suitable for pre-treatment of stained fabrics, and a rinse added fabric softener composition. Alternatively, the detergent composition of the present invention may be used in general household hard surface cleaning operations, or be formulated for hand or machine dishwashing operations.

In a specific aspect, the invention provides a detergent additive comprising the enzyme of the invention. The detergent additive as well as the detergent composition may comprise one or more other enzymes such as a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in the detergent composition.

Other Uses

Subtilisin-like proteins are widely used in the leather industry. The biotreatment of leather using an enzymatic approach is preferable as it offers several advantages (Varela H., Ferrari M.D., Belobradjic L., Weyrauch R., Loperena M. L. (1996). *World J. Microbiol. Biotechnol.* 12:643-645).

The present invention may also be used in contact lens cleaning and disinfecting systems (See e.g. U.S. Pat. No. 6,358,897, U.S. Pat. No. 6,139,646).

In addition, the present invention may be used in topical treatments, in treatment of skin scarring and skin infections (Jung H. (1998) *Facial Plast. Surg.* 14(4):255-257).

In the food industry, for example, aminopeptidases have been used to increase the speed of the cheese maturing process. Many proteases have been used in the preparation of protein hydrolysates of high nutritional value.

One of the least explored areas for the use of proteases is the silk industry and only a few patents have been filed describing the use of proteases for the degumming of silk (see e.g. U.S. Pat. No. 6,080,689).

Recently, the use of alkaline protease in the management of wastes from various food-processing industries and household activities opened up a new era in the use of proteases in waste management (Daley P. G. (1994). *Bioresour. Technol.* 48:265-267).

Another less known application sector is the use of proteases for cleaning of membrane systems (U.S. Pat. No. 6,387,189). The proteases of the present invention can be used in any one or more of the applications mentioned herein.

Materials and Methods

The present invention is further exemplified by the following non-limiting examples.

Example 1

Protein Purification and Mass Spectrometric Analysis

Briefly, the *Polaribacter* strain 3-17 was grown in an aerated fermentor for 48 hours at 10° C. After precipitation of the culture, 1 M (NH4)2SO4 was added to the supernatant fraction and this was incubated with Phenyl-sepharose Fast Flow resin (Pharmacia Biotech) at 4° C. for 2 hr. The resin with absorbed protease was packed in a chromatographic column and then subject to hydrophobic interaction chromatography. 0.05 M Tris/HCl, 2 mM CaCl2, 1 M (NH4)SO4 pH 7.5 was used as the equilibrating buffer and 0.05 M Tris/HCl, 2 mM CaCl2, 7.5% 2-Propanol pH 7.5 was used as elution buffer. The chromatographic fraction with protease activity was desalted in a Sephadex G-25 column, and subjected to an affinity chromatography with bacitracin-Sepharose, which was performed by the method of Stepanov and Rudenskaya (Stepanov V. M., Rudenskaya G. N. (1983). J Appl Biochem. 5:420-428). To this purified protein a subtilisin-like activity assay was carried out at 20° C., the protein in the fraction with the higher protease activity was analyzed by mass spectrometry LC/MS/MS LCQ Deca XP (Ion Trap) by CHUL Research Center, Quebec, and from this analysis the sequence of some peptides was calculated from its MS/MS spectra (SEQ ID NOS: 3, 4, 5).

Example 2

DNA Cloning of Characterized Protein of the Invention

Nucleic Acid Manipulation

Psychrophilic bacteria were isolated from seawater collected at Frei Montalva Base (Lat 62° 11" S Long 58° 58" W), King George Island, Chilean Antarctic. Cells for DNA manipulation were harvested by centrifugation at 4° C. after 4 days of cultivation in marine medium 2216 (BD 279110) with shaking at 4° C. DNA manipulation was carried out as described in Sambrook et al. Molecular Cloning, a Laboratory Manual (Cold Spring Harbor Press, 1989). PCR products were purified from agarose gel after electrophoresis by QIAEXII supplied by QIAGEN Inc. (Calif., USA). PCR-purified products were cloned into the pGEM-T Easy vector (Promega, Wis., USA), and sequenced by Macrogen (Korea). Primers and restriction enzymes were supplied by Invitrogen (CA, USA) and New England Biolabs (MA, USA), respectively. Taq polymerase and Elongase were purchased from Promega and Invitrogen, respectively.

Degenerated Primer Design

Three degenerated primers (SEQ ID NOS: 6, 7, 8) were designed based on the previously calculated amino acid sequence of the peptides (SEQ ID NOS: 3, 4, 5). The sense primer SEQ ID NO: 6 and the antisense primer SEQ ID NO: 7 were able to amplify a central region of the gene encoding the subtilisin-like proteins (SEQ ID NO: 9). The amplifications were cloned in a pGEM-T system (Promega) and selected clones were automatically sequenced. To complete the rest of the subtilisin-like encoding gene, a new method of genome walking was implemented.

Genome Walking Method

1) Construction of Oligo-Cassette:

A double-stranded oligo-cassette AdaptT adapter was constructed by annealing of the two unphosphorylated primers AdaptF and AdaptR (SEQ ID NOS: 10, 11). Annealing was performed by heating the primers (10 µM) in a boiling water bath, and then slowly cooling to room temperature. This cassette has a 3' overhanging thymidine.

2) Construction of Oligo-Cassette Libraries:

For construction of DNA fragments linked to the oligo-cassette AdaptT, 1 µg of genomic DNA was digested with 10 activity units of a restriction enzyme (HindIII, XbaI, EcoRV, EcoRI, Sau3AI, PvuII) and 2 µl of 10× enzyme reaction buffer in 20 µl reaction volume. To complete the 3' recessive end of the fragments and to add a 3' overhanging adenine, 500 ng of the digested and purified DNA were incubated with 5 activity units of Taq DNA polymerase, 1 µl of 10 mM dNTPs mix (dATP, dTTP, dGTP and dCTP) and 5 µl of 10× thermophilic DNA polymerase buffer in 50 µl total volume, at 70° C. for 45 min. 7 µl of this mixture was incubated with 15 µmoles of AdaptT oligo-cassette, 1 unit T4 DNA ligase (Invitrogen) and 2 µl of 5× ligase buffer, in a total volume of 10 µl. The ligation reaction was incubated at 16° C. overnight.

3) First Round of PCR

The amplification reaction was performed in a volume of 50 µl with 1× Elongase mix buffer, 1.9 mM $MgCl_2$, 0.2 mM dNTPs, 0.5 µM first specific primer (designed from the known sequence of the target gene (SEQ ID NO: 9); it should be a forward primer to amplify the 3' end (SEQ ID NO: 13) or a reverse primer to amplify the 5' end (SEQ ID NO: 14)), 5 µl of the ligated DNA diluted 10 fold and 1 µl of Elongase. The thermal cycling conditions were: 1 cycle at 94° C. for 1 min, 20 cycles of 94° C. for 32 sec and 68° C. for 5 min, and 1 final additional cycle at 70° C. for 7 min. Reactions were carried out in an Eppendorf Master Cycler Gradient (HA, GE). The PCR product was diluted 10 fold and 3 μl were used as a DNA template for second PCR.

4) Second Round of PCR

The second amplification reaction was performed in a total volume of 50 μl of 1× elongase mix buffer, where the final concentrations were: 1.9 mM MgCl$_2$, 0.2 mM dNTPs, 0.5 μM second specific primer (designed from the known sequence of the target gene (SEQ ID NO: 9); it should be a forward primer to amplify the 3' end (SEQ ID NO: 15) or a reverse primer to amplify the 5' end (SEQ ID NO: 16)), 0.2 μM oligo-cassatte-specific primer AdaptF2 (SEQ ID NOS: 12), 3 μl of the diluted product from the first PCR and 1 μl of Elongase. The thermal cycling conditions were: 1 cycle at 94° C. for 1 min, 35 cycles of 94° C. for 32 sec and 68° C. for 5 min, and 1 final additional cycle at 70° C. for 7 min.

5) Construction of the Complete Nucleic Acid Sequence:

The amplifications of the second PCR (5' and 3') were cloned in a pGEM-T system (Promega) and selected clones were automatically sequenced. By overlapping of the sequences previously amplified it was possible to obtain the whole nucleotide sequence of the subtilisin-like encoding gene. In order to be sure about the correct sequence of the gene, two primers were designed from the ends of the gene and another amplification was performed using a high-fidelity DNA polymerase. The amplifications were cloned in a pGEM-T system (Promega) and selected clones were automatically sequenced.

Example 3

Construction of Expression Vector and Expression of the Protein of the Invention With the sequences obtained with the new genome walking method, two primers (SEQ ID NOS.: 17, 18) were designed and a final PCR was carried out. In addition, cloning and sequencing of the complete gene which encodes the purified protein of the present invention were completed. Eight clones were analyzed, representing the same gene (SEQ ID NO.: 1). The cold adapted subtilisin-like protein was expressed in *E. coli* using the NcoI and Xho I sites of a pET22b vector provided by Novagen. The pET vector places the recombinant protein under the control of bacteriophage T7 transcription and translation signals. Once established in a non-expression host, *E. coli* DH5α, the plasmid was then transferred to an expression host, *E. coli* BL21 (DE3) pLYS S having a chromosomal copy of the T7 polymerase gene under lacUV5 control. Expression was induced by the addition of IPTG.

Sequences

The nucleic acid sequences described herein, and consequently the protein sequences derived therefrom, have been carefully sequenced. However, those of ordinary skill will recognize that nucleic acid sequencing technology can be susceptible to some inadvertent error. Those of ordinary skill in the relevant arts are capable of validating or correcting these sequences based on the ample description herein of methods of isolating the nucleic acid sequences in question and such modifications that are made readily available by the present disclosure are encompassed by the present invention. Furthermore, those sequences reported herein are believed to define functional biological macromolecules within the invention whether or not later clarifying studies identify sequencing errors.

What is claimed is:

1. An isolated nucleic acid vector comprising a nucleotide sequence having at least 95% identity to SEQ ID NO: 1 and with 100% identity at positions 361-423, 466-528 and 1039-1101 of SEQ ID NO: 1, or a degenerative variant thereof, wherein said isolated nucleic acid encodes a polypeptide with subtilisin-like activity capable of cleaving Succinyl-Ala-Ala-Pro-Phe↓p-Nitroanilide.

2. The isolated nucleic acid vector as claimed in claim 1, comprising the nucleotide sequence as is shown in SEQ ID NO: 1 or a degenerative variant thereof.

3. An isolated nucleic acid vector comprising a sequence that encodes a polypeptide the amino acid sequence of which is at least 95% identical to SEQ ID NO: 2, wherein the polypeptide has subtilisin-like activity capable of cleaving Succinyl-Ala-Ala-Pro-Phe↓p-Nitroanilide.

4. The nucleic acid vector according to claim 3, wherein the amino acid sequence of the polypeptide is at least 97% identical to SEQ ID NO: 2.

5. The nucleic acid vector of claim 1, wherein the vector is an expression vector having the nucleotide sequence linked to an expression control sequence.

6. The nucleic acid vector of claim 3, wherein the vector is an expression vector having the nucleotide sequence linked to an expression control sequence.

7. A transformed cell comprising the nucleic acid vector as claimed in claim 1.

8. A transformed cell comprising the nucleic acid vector as claimed in claim 3.

9. A method of preparing a protein comprising the steps of: transforming a cell with the expression vector as claimed in claim 5, growing the transformed cell in culture; and isolating the protein encoded in the vector as claimed in claim 5.

10. A method of preparing a protein comprising the steps of: transforming a cell with the expression vector as claimed in claim 6, growing the transformed cell in culture; and isolating the protein encoded in the vector as claimed in claim 6.

11. A transformed cell comprising the nucleic acid vector as claimed in claim 2.

12. A transformed cell comprising the nucleic acid vector as claimed in claim 4.

13. The nucleic acid vector according to claim 3, wherein the amino acid sequence of the polypeptide has at least 99% identity to SEQ ID NO: 2.

* * * * *

SEQUENCE LISTING

```
<160> NUMBER OF SEQ ID NOS: 19

<210> SEQ ID NO 1
<211> LENGTH: 3390
<212> TYPE: DNA
<213> ORGANISM: Polaribacter sp.

<400> SEQUENCE: 1
atgaaaaaaa ggtacattaa tttacttctt acaattggag tttttatgat ttctgctttc      60
aacatgaatg ctcaaaaaca agaagaatta acaaaaatta gcagtaagta caatcaagaa     120
aaacttacta cgttaaaaaa tgattttaaa cagaaggctt ctttagataa acaaaatgca     180
attacaattg caaagagtaa aggatggaaa actagattta ccaataagaa aggtgaatta     240
ttagaaattc aaaaagtagt aaatggaaaa ccaatttatt ataccacttt taatgttgca     300
gccgcaaaat ctacaagaac aaatcattta aacaacggtg gttctttagg cttaaatttg     360
atggggcaaa atatgactgc tcatgtttgg gatggcggat tagcaagagc atctcaccaa     420
gaatatgatg gtgctggtgg tacaaataga ttctctattg gagatggcac aacagcttta     480
cactaccatt ctgctcacgt aacaggtaca attatggctt ctggtgttgt tgcaaatgca     540
aaaggaatgg cgcctcatgc aagtgctgtt ggttatgatt ggaataatga cacttctgaa     600
gctataaacg cagcttcaaa cggaatgtta gtttctaatc attcttatgg ttttgctaca     660
agaaatgcac aaggtcaacc tcaacttcca gattattatt ttggagggta cattacagac     720
```

```
tctagagatt gggataacat tatgtttaat gcaccaaact atttaatggt tgttgcagca      780
ggaaatgatg gaaatgataa ttctgctaat ggtgctccat tagctggaaa ttcttcttat      840
gacaaattat ctggtcatgc aactgcaaaa aacggtatgg ttgttgccaa cgcaaatgat      900
gctaatatag atgtaaatgg aaacctgctt tccgttacta taaattcttc tagtagtgaa      960
ggaccaacag atgattaccg tattaaacca gatattactg gaaacggaac atctgtatat     1020
tctacttatt cgtctagtaa tacagctat aatagtacta ctggtacttc tatggcatcg      1080
ccaaatgttg cgggtacact attaatttta caacaacatg ctaacaatgt tagaggttcg     1140
tttattaaag cttcaacttt aaaaggaatt gctttacata ctgcagatga cgcaggttct     1200
aatggaccag atgcaatttt tggctgggga ttaatgaatg ctaaaagagc tgctgtagca     1260
attactcaaa acggtactga atctaagatt gaagaactaa ctttatctag cagacaaacg     1320
tatcaaatta ctgtagatgc tgatggagtt aatgatttaa tggcttctat ttcttggaca     1380
gatagagctg gaactgcaac tactacagca aattcaagta ctgctgtttt agtaaatgat     1440
ttagatatta gagtttctaa aaacggaaca acctatactc cttggagatt aacaggagta     1500
acaacaaatg gaaaaggtga taatactgta gatccttatg aaagagttga tgttgctaac     1560
gcttcaggaa cttatacaat tactgtaact cataaaggtt ctttaactgg cggaagtcaa     1620
aattattcat taattgtaac tggtttagca ggaacgcctg ttgtatgtaa tgcaacaatc     1680
ccttctaatc ttactgttga tgaatctgga gcttcaaccg caactgtttc ttggaatact     1740
gtcgctggaa cttcttacga ttttagatac cgcaaaacag gcacgtcaac ctggacaact     1800
tctgctgttg cgggaacttc ggtttcttta acaggattat ctactcaaac ttcttatcaa     1860
actcaagtaa gaagcaaatg tcctaataat tctacctcag catattctag tgctgttagt     1920
tttacaactt cagatgttca gcttaattat tgtgcttcaa acggaaatag tgttgcagat     1980
gaatacataa gtaaagtagt tcttggaggt ataaacaata caaccggagc ttcatcaagc     2040
ggatacgctg attcacctc tcaatctaca agtttaacga aaggagtttc ttcaacaatt     2100
acaattaccc caacctgggc aggagcttca tataacgaag ttatgctgt atttattgac     2160
tataataagg atggtgattt tacagataat ggagaaaccg tttggacaaa aatagcttct     2220
aaaacaaaac ctgttagcgg ttcatttact gtgccaacat ctgcaactac aggagcaact     2280
agaatgcgtg tagtaatgca atacaatacc gtacctgctg cttgtggaac ctataattat     2340
ggtgaaacag aagattatac tgtaaacata accggaagta gtgcagatac aatagcacca     2400
actgcgccta caaatgtatc agcttcagct attacccaaa ctacggctac attatcttgg     2460
acagcatcta cagataacgt aggagtagca ggatacgaga tatttagtaa cggaacaagt     2520
gttgaaccg taacagcaac ttctgctaac ataactggtt taacagcaaa tacttcatac     2580
tcatatacta taaaagctaa tgatgcagca gagaacacat ctaactcaag taatagtgtg     2640
tcatttacaa cattaggaag tacgctagta tattgttcct ctaaaggaaa tagagtaact     2700
tatgaatgga tcgattatgt gagttttgga ggaatgacaa atacaactgc agcaaacgca     2760
ggatatggag attttacttc aaaaacagca acagtatcta aggaagtga taaccaactg     2820
ataataagtg caggtttgc aagtactgca tatacagaac attgggcagt ttggatcgat     2880
tttaatcaaa acgaactttt tgaagaaagc gaaaagtta cttctggttc ttcttctagt     2940
gcggctaatt taactgcaac tatttcaatt ccttcttcag ctaatactgg tcaaacaaga     3000
atgcgtgttt caatgaaata caatagtgcg caaacagctt gtgaaacatt ttctgatgga     3060
gaagtagaag actacacagt aaatattaca aacgctacag caaattatac tacatttatt     3120
```

```
aatactaatt ctaaaaatga attaggaaat gaaagtaaag cattcgattt tacagtatat   3180
cctaaccctg taaaaggaac tgttttaaac attcacttaa atgatgctag agaagttaac   3240
tttgcaatta caaacatgtt agggcaaacc ttaaaaagtg gtattttaac aaaacaacct   3300
atagatgtta gtactattaa aacaggtgtt tacatgttag aaataactga tggacaaaag   3360
tctgttgtta aaaattcgt tagacaataa                                    3390
```

<210> SEQ ID NO 2
<211> LENGTH: 1129
<212> TYPE: PRT
<213> ORGANISM: Polaribacter sp.

<400> SEQUENCE: 2

```
Met Lys Lys Arg Tyr Ile Asn Leu Leu Leu Thr Ile Gly Val Phe Met
1               5                   10                  15

Ile Ser Ala Phe Asn Met Asn Ala Gln Lys Gln Glu Glu Leu Thr Lys
            20                  25                  30

Ile Ser Ser Lys Tyr Asn Gln Glu Lys Leu Thr Thr Leu Lys Asn Asp
        35                  40                  45

Phe Lys Gln Lys Ala Ser Leu Asp Lys Gln Asn Ala Ile Thr Ile Ala
    50                  55                  60

Lys Ser Lys Gly Trp Lys Thr Arg Phe Thr Asn Lys Lys Gly Glu Leu
65                  70                  75                  80

Leu Glu Ile Gln Lys Val Val Asn Gly Lys Pro Ile Tyr Tyr Thr Thr
                85                  90                  95

Phe Asn Val Ala Ala Ala Lys Ser Thr Arg Thr Asn His Leu Asn Asn
            100                 105                 110

Gly Gly Ser Leu Gly Leu Asn Leu Met Gly Gln Asn Met Thr Ala His
        115                 120                 125

Val Trp Asp Gly Gly Leu Ala Arg Ala Ser His Gln Glu Tyr Asp Gly
    130                 135                 140

Ala Gly Gly Thr Asn Arg Phe Ser Ile Gly Asp Gly Thr Thr Ala Leu
145                 150                 155                 160

His Tyr His Ser Ala His Val Thr Gly Thr Ile Met Ala Ser Gly Val
                165                 170                 175

Val Ala Asn Ala Lys Gly Met Ala Pro His Ala Ser Ala Val Gly Tyr
            180                 185                 190

Asp Trp Asn Asn Asp Thr Ser Glu Ala Ile Asn Ala Ala Ser Asn Gly
        195                 200                 205

Met Leu Val Ser Asn His Ser Tyr Gly Phe Ala Thr Arg Asn Ala Gln
    210                 215                 220

Gly Gln Pro Gln Leu Pro Asp Tyr Tyr Phe Gly Gly Tyr Ile Thr Asp
225                 230                 235                 240

Ser Arg Asp Trp Asp Asn Ile Met Phe Asn Ala Pro Asn Tyr Leu Met
                245                 250                 255

Val Val Ala Ala Gly Asn Asp Gly Asn Asp Asn Ser Ala Asn Gly Ala
            260                 265                 270

Pro Leu Ala Gly Asn Ser Ser Tyr Asp Lys Leu Ser Gly His Ala Thr
        275                 280                 285

Ala Lys Asn Gly Met Val Val Ala Asn Ala Asn Asp Ala Asn Ile Asp
    290                 295                 300

Val Asn Gly Asn Leu Leu Ser Val Thr Ile Asn Ser Ser Ser Ser Glu
305                 310                 315                 320

Gly Pro Thr Asp Asp Tyr Arg Ile Lys Pro Asp Ile Thr Gly Asn Gly
                325                 330                 335
```

```
Thr Ser Val Tyr Ser Thr Tyr Ser Ser Asn Thr Ala Tyr Asn Ser
            340                 345                 350

Thr Thr Gly Thr Ser Met Ala Ser Pro Asn Val Ala Gly Thr Leu Leu
        355                 360                 365

Ile Leu Gln Gln His Ala Asn Asn Val Arg Gly Ser Phe Ile Lys Ala
    370                 375                 380

Ser Thr Leu Lys Gly Ile Ala Leu His Thr Ala Asp Asp Ala Gly Ser
385                 390                 395                 400

Asn Gly Pro Asp Ala Ile Phe Gly Trp Gly Leu Met Asn Ala Lys Arg
                405                 410                 415

Ala Ala Val Ala Ile Thr Gln Asn Gly Thr Glu Ser Lys Ile Glu Glu
                420                 425                 430

Leu Thr Leu Ser Ser Arg Gln Thr Tyr Gln Ile Thr Val Asp Ala Asp
            435                 440                 445

Gly Val Asn Asp Leu Met Ala Ser Ile Ser Trp Thr Asp Arg Ala Gly
    450                 455                 460

Thr Ala Thr Thr Thr Ala Asn Ser Ser Thr Ala Val Leu Val Asn Asp
465                 470                 475                 480

Leu Asp Ile Arg Val Ser Lys Asn Gly Thr Thr Tyr Thr Pro Trp Arg
                485                 490                 495

Leu Thr Gly Val Thr Thr Asn Gly Lys Gly Asp Asn Thr Val Asp Pro
            500                 505                 510

Tyr Glu Arg Val Asp Val Ala Asn Ala Ser Gly Thr Tyr Thr Ile Thr
                515                 520                 525

Val Thr His Lys Gly Ser Leu Thr Gly Gly Ser Gln Asn Tyr Ser Leu
530                 535                 540

Ile Val Thr Gly Leu Ala Gly Thr Pro Val Val Cys Asn Ala Thr Ile
545                 550                 555                 560

Pro Ser Asn Leu Thr Val Asp Glu Ser Gly Ala Ser Thr Ala Thr Val
            565                 570                 575

Ser Trp Asn Thr Val Ala Gly Thr Ser Tyr Asp Phe Arg Tyr Arg Lys
            580                 585                 590

Thr Gly Thr Ser Thr Trp Thr Thr Ser Ala Val Ala Gly Thr Ser Val
            595                 600                 605

Ser Leu Thr Gly Leu Ser Thr Gln Thr Ser Tyr Gln Thr Gln Val Arg
    610                 615                 620

Ser Lys Cys Pro Asn Asn Ser Thr Ser Ala Tyr Ser Ser Ala Val Ser
625                 630                 635                 640

Phe Thr Thr Ser Asp Val Gln Leu Asn Tyr Cys Ala Ser Asn Gly Asn
                645                 650                 655

Ser Val Ala Asp Glu Tyr Ile Ser Lys Val Val Leu Gly Gly Ile Asn
                660                 665                 670

Asn Thr Thr Gly Ala Ser Ser Ser Gly Tyr Ala Asp Tyr Thr Ser Gln
            675                 680                 685

Ser Thr Ser Leu Thr Lys Gly Val Ser Ser Thr Ile Thr Ile Thr Pro
    690                 695                 700

Thr Trp Ala Gly Ala Ser Tyr Asn Glu Gly Tyr Ala Val Phe Ile Asp
705                 710                 715                 720

Tyr Asn Lys Asp Gly Asp Phe Thr Asp Asn Gly Glu Thr Val Trp Thr
                725                 730                 735

Lys Ile Ala Ser Lys Thr Lys Pro Val Ser Gly Ser Phe Thr Val Pro
                740                 745                 750

Thr Ser Ala Thr Thr Gly Ala Thr Arg Met Arg Val Val Met Gln Tyr
```

```
                755                 760                 765
Asn Thr Val Pro Ala Ala Cys Gly Thr Tyr Asn Tyr Gly Glu Thr Glu
770                 775                 780

Asp Tyr Thr Val Asn Ile Thr Gly Ser Ser Ala Asp Thr Ile Ala Pro
785                 790                 795                 800

Thr Ala Pro Thr Asn Val Ser Ala Ser Ala Ile Thr Gln Thr Ala
                805                 810                 815

Thr Leu Ser Trp Thr Ala Ser Thr Asp Asn Val Gly Val Ala Gly Tyr
                820                 825                 830

Glu Ile Phe Ser Asn Gly Thr Ser Val Gly Thr Val Thr Ala Thr Ser
                835                 840                 845

Ala Asn Ile Thr Gly Leu Thr Ala Asn Thr Ser Tyr Ser Tyr Thr Ile
850                 855                 860

Lys Ala Asn Asp Ala Ala Glu Asn Thr Ser Asn Ser Ser Asn Ser Val
865                 870                 875                 880

Ser Phe Thr Thr Leu Gly Ser Thr Leu Val Tyr Cys Ser Ser Lys Gly
                885                 890                 895

Asn Arg Val Thr Tyr Glu Trp Ile Asp Tyr Val Ser Phe Gly Gly Met
                900                 905                 910

Thr Asn Thr Thr Ala Ala Asn Ala Gly Tyr Gly Asp Phe Thr Ser Lys
                915                 920                 925

Thr Ala Thr Val Ser Lys Gly Ser Asp Asn Gln Leu Ile Ile Ser Ala
930                 935                 940

Gly Phe Ala Ser Thr Ala Tyr Thr Glu His Trp Ala Val Trp Ile Asp
945                 950                 955                 960

Phe Asn Gln Asn Gly Thr Phe Glu Glu Ser Glu Lys Val Thr Ser Gly
                965                 970                 975

Ser Ser Ser Ser Ala Ala Asn Leu Thr Ala Thr Ile Ser Ile Pro Ser
                980                 985                 990

Ser Ala Asn Thr Gly Gln Thr Arg Met Arg Val Ser Met Lys Tyr Asn
                995                1000                1005

Ser Ala Gln Thr Ala Cys Glu Thr Phe Ser Asp Gly Glu Val Glu
                1010                1015                1020

Asp Tyr Thr Val Asn Ile Thr Asn Ala Thr Ala Asn Tyr Thr Thr
1025                1030                1035

Phe Ile Asn Thr Asn Ser Lys Asn Glu Leu Gly Asn Glu Ser Lys
1040                1045                1050

Ala Phe Asp Phe Thr Val Tyr Pro Asn Pro Val Lys Gly Thr Val
1055                1060                1065

Leu Asn Ile His Leu Asn Asp Ala Arg Glu Val Asn Phe Ala Ile
1070                1075                1080

Thr Asn Met Leu Gly Gln Thr Leu Lys Ser Gly Ile Leu Thr Lys
1085                1090                1095

Gln Pro Ile Asp Val Ser Thr Ile Lys Thr Gly Val Tyr Met Leu
1100                1105                1110

Glu Ile Thr Asp Gly Gln Lys Ser Val Val Lys Lys Phe Val Arg
1115                1120                1125

Gln
```

<210> SEQ ID NO 3
<211> LENGTH: 13
<212> TYPE: PRT
<213> ORGANISM: Polaribacter sp.
<220> FEATURE:
<221> NAME/KEY: MISC_FEATURE

```
<222> LOCATION: (1)..(4)
<223> OTHER INFORMATION: Xaa is Leu or Ile

<400> SEQUENCE: 3

Xaa Xaa Xaa Xaa Leu Gln Gln His Ala Asn Asn Val Arg
1               5                   10

<210> SEQ ID NO 4
<211> LENGTH: 8
<212> TYPE: PRT
<213> ORGANISM: Polaribacter sp.
<220> FEATURE:
<221> NAME/KEY: MISC_FEATURE
<222> LOCATION: (8)..(8)
<223> OTHER INFORMATION: Xaa is Leu or Ile

<400> SEQUENCE: 4

Asn Ala Ser Gly Thr Tyr Thr Xaa
1               5

<210> SEQ ID NO 5
<211> LENGTH: 7
<212> TYPE: PRT
<213> ORGANISM: Polaribacter sp.

<400> SEQUENCE: 5

Asn Gly Thr Thr Tyr Thr Pro
1               5

<210> SEQ ID NO 6
<211> LENGTH: 27
<212> TYPE: DNA
<213> ORGANISM: Artificial Sequence
<220> FEATURE:
<223> OTHER INFORMATION: Degenerated polymerase chain reaction primer
<220> FEATURE:
<221> NAME/KEY: misc_feature
<222> LOCATION: (1)..(1)
<223> OTHER INFORMATION: w is a or t
<220> FEATURE:
<221> NAME/KEY: misc_feature
<222> LOCATION: (3)..(3)
<223> OTHER INFORMATION: w is a or t
<220> FEATURE:
<221> NAME/KEY: misc_feature
<222> LOCATION: (15)..(15)
<223> OTHER INFORMATION: w is a or t
<220> FEATURE:
<221> NAME/KEY: misc_feature
<222> LOCATION: (18)..(18)
<223> OTHER INFORMATION: y is c or t
        220>
<221> NAME/KEY: misc_feature
<222> LOCATION: (21)..(21)
<223> OTHER INFORMATION: y is c or t
<220> FEATURE:
<221> NAME/KEY: misc_feature
<222> LOCATION: (24)..(24)
<223> OTHER INFORMATION: w is a or t

<400> SEQUENCE: 6
wtwcaacaac atgcwaayaa ygtwaga                                           27

<210> SEQ ID NO 7
<211> LENGTH: 21
<212> TYPE: DNA
<213> ORGANISM: Artificial Sequence
<220> FEATURE:
<223> OTHER INFORMATION: Degenerated polymerase chain reaction primer
<220> FEATURE:
<221> NAME/KEY: misc_feature
<222> LOCATION: (1)..(1)
```

```
<223> OTHER INFORMATION: w is a or t
<220> FEATURE:
<221> NAME/KEY: misc_feature
<222> LOCATION: (4)..(4)
<223> OTHER INFORMATION: r is a or g
<220> FEATURE:
<221> NAME/KEY: misc_feature
<222> LOCATION: (7)..(7)
<223> OTHER INFORMATION: w is a or t
<220> FEATURE:
<221> NAME/KEY: misc_feature
<222> LOCATION: (10)..(10)
<223> OTHER INFORMATION: w is a or t
<220> FEATURE:
<221> NAME/KEY: misc_feature
<222> LOCATION: (13)..(13)
<223> OTHER INFORMATION: w is a or t
<220> FEATURE:
<221> NAME/KEY: misc_feature
<222> LOCATION: (16)..(16)
<223> OTHER INFORMATION: w is a or t
<220> FEATURE:
<221> NAME/KEY: misc_feature
<222> LOCATION: (19)..(19)
<223> OTHER INFORMATION: r is a or g

<400> SEQUENCE: 7
wgtrtawgtw ccwgawgcrt t                                              21

<210> SEQ ID NO 8
<211> LENGTH: 21
<212> TYPE: DNA
<213> ORGANISM: Artificial Sequence
<220> FEATURE:
<223> OTHER INFORMATION: Degenerated polymerase chain reaction primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 8
aayggnacna cntayacncc n                                              21

<210> SEQ ID NO 9
<211> LENGTH: 471
<212> TYPE: DNA
<213> ORGANISM: Polaribacter sp.

<400> SEQUENCE: 9
ttacaacaac atgctaacaa tgttagaggt tcgtttatta aagcttcaac tttaaaagga    60
attgctttac atactgcaga tgacgcaggt tctaatggac cagatgcaat ttttggctgg   120
ggattaatga atgctaaaag agctgctgta gcaattactc aaaacggtac tgaatctaag   180
attgaagaac taactttatc tagcagacaa acgtatcaaa ttactgtaga tgctgatgga   240
gttaatgatt taatggcttc tatttcttgg acagatagag ctggaactgc aactactaca   300
```

```
gcaaattcaa gtactgctgt tttagtaaat gatttagata ttagagtttc taaaaacgga    360
acaacctata ctccttggag attaacagga gtaacaacaa atggaaaagg tgataatact    420
gtagatcctt atgaaagagt tgatgttgct aacgcttcag gaacttatac a             471
```

```
<210> SEQ ID NO 10
<211> LENGTH: 29
<212> TYPE: DNA
<213> ORGANISM: Artificial Sequence
<220> FEATURE:
<223> OTHER INFORMATION: Polymerase chain reaction primer

<400> SEQUENCE: 10
ctaggccacg cgtcgactag tactagctt                                       29

<210> SEQ ID NO 11
<211> LENGTH: 28
<212> TYPE: DNA
<213> ORGANISM: Artificial Sequence
<220> FEATURE:
<223> OTHER INFORMATION: Polymerase chain reaction primer

<400> SEQUENCE: 11
agctagtact agtcgacgcg tggcctag                                        28

<210> SEQ ID NO 12
<211> LENGTH: 23
<212> TYPE: DNA
<213> ORGANISM: Artificial Sequence
<220> FEATURE:
<223> OTHER INFORMATION: Polymerase chain reaction primer

<400> SEQUENCE: 12
cacgcgtcga ctagtactag ctt                                             23

<210> SEQ ID NO 13
<211> LENGTH: 26
<212> TYPE: DNA
<213> ORGANISM: Artificial Sequence
<220> FEATURE:
<223> OTHER INFORMATION: Polymerase chain reaction primer

<400> SEQUENCE: 13
ctaatggacc agatgcaatt tttggc                                          26

<210> SEQ ID NO 14
<211> LENGTH: 31
<212> TYPE: DNA
<213> ORGANISM: Artificial Sequence
<220> FEATURE:
<223> OTHER INFORMATION: Polymerase chain reaction primer

<400> SEQUENCE: 14
gctgtagtag ttgcagttcc agctctatct g                                    31

<210> SEQ ID NO 15
<211> LENGTH: 32
<212> TYPE: DNA
<213> ORGANISM: Artificial Sequence
<220> FEATURE:
<223> OTHER INFORMATION: Polymerase chain reaction primer

<400> SEQUENCE: 15
gaaagagttg atgttgctaa cgcttcagga ac                                   32

<210> SEQ ID NO 16
```

```
<211> LENGTH: 29
<212> TYPE: DNA
<213> ORGANISM: Artificial Sequence
<220> FEATURE:
<223> OTHER INFORMATION: Polymerase chain reaction primer

<400> SEQUENCE: 16
ccattagaac ctgcgtcatc tgcagtatg                                          29

<210> SEQ ID NO 17
<211> LENGTH: 35
<212> TYPE: DNA
<213> ORGANISM: Artificial Sequence
<220> FEATURE:
<223> OTHER INFORMATION: Polymerase chain reaction primer

<400> SEQUENCE: 17
catatgaaaa aaaggtacat taatttactt cttac                                   35

<210> SEQ ID NO 18
<211> LENGTH: 32
<212> TYPE: DNA
<213> ORGANISM: Artificial Sequence
<220> FEATURE:
<223> OTHER INFORMATION: Polymerase chain reaction primer

<400> SEQUENCE: 18
ctcgagttgt ctaacgaatt ttttaacaac ag                                      32

<210> SEQ ID NO 19
<211> LENGTH: 897
<212> TYPE: DNA
<213> ORGANISM: Polaribacter sp.

<400> SEQUENCE: 19
caatggagga gactctgatc cagccatgcc gcgtgtagga agaatgccct atgggttgta         60
aactactttt atacaggaag aaacactagt atgtatacta gcttgacggt actgtaagaa        120
taaggaccgg ctaactccgt gccagcagcc gcggtaatac ggagggtcca agcgttatcc        180
ggaatcattg ggtttaaagg gtccgcaggc ggtcaattaa gtcagaggtg aaatcccata        240
gcttaactat ggaactgcct ttgatactgg ttgacttgag tcatatggaa gtagatagaa        300
tgtgtagtgt agcggtgaaa tgcatagata ttacacagaa taccgattgc gaaggcagtc        360
tactacgtat gtactgacgc tgagggacga aagcgtgggg agcgaacagg attagatacc        420
ctggtagtcc acgccgtaaa cgatggatac tagttgttgg gatttatctc agtgactaag        480
cgaaagtgat aagtatccca cctggggagt acgtcgcaa gactgaaact caaaggaatt        540
gacgggggcc cgcacaagcg gtggagcatg tggtttaatt cgatgatacg cgaggaacct        600
taccagggct taaatgtagt ctgacagctt tagagataga gttttcttcg gacagattac        660
aaggtgctgc atggttgtcg tcagctcgtg ccgtgaggtg tcaggttaag tcctataacg        720
agcgcaaccc ctgtcgttag ttgccagcat gttatgatgg ggactctaac gagactgcct        780
acgcaagtag agaggaaggt ggggatgacg tcaaatcatc acggccctta cgtcctgggc        840
cacacacgtg ctacaatggt atggacaatg agcagccatc ggcaacagag agcgaat           897
```